US007060438B1

(12) United States Patent
Mougin et al.

(10) Patent No.: US 7,060,438 B1
(45) Date of Patent: Jun. 13, 2006

(54) METHOD FOR ANALYZING A PATIENT'S GENETIC PREDIPOSITION TO AT LEAST ONE DISEASE AND AMPLIFICATION ADAPTED TO SUCH A METHOD

(75) Inventors: Bruno Mougin, Lyons (FR); Jean-Marie Tiercy, Chenes bou Geries (CH)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/979,088

(22) PCT Filed: May 19, 2000

(86) PCT No.: PCT/FR00/01385

§ 371 (c)(1),
(2), (4) Date: Jan. 14, 2002

(87) PCT Pub. No.: WO00/71750

PCT Pub. Date: Nov. 30, 2000

(30) Foreign Application Priority Data

May 20, 1999  (FR) ................................... 99 06599
Dec. 6, 1999   (FR) ................................... 99 15314

(51) Int. Cl.
C12Q 1/68   (2006.01)
C12P 19/34  (2006.01)
(52) U.S. Cl. ......................................... 435/6; 435/91.2
(58) Field of Classification Search .................. 435/6, 435/91.1, 91.2; 536/23.1, 24.32, 24.33
See application file for complete search history.

(56) References Cited

U.S. PATENT DOCUMENTS

| 5,468,611 A |   | 11/1995 | Baxter-Lowe et al. |          |
|-------------|---|---------|--------------------|----------|
| 5,567,809 A | * | 10/1996 | Apple et al.       | 536/24.3 |
| 5,939,542 A |   |  8/1999 | Kawai et al.       |          |
| 5,976,789 A | * | 11/1999 | Allibert et al.    | 435/6    |

FOREIGN PATENT DOCUMENTS

| AU | 717296       | 12/1996 |
| EP | 0 875 582 A  | 11/1998 |
| EP | 0 887 423 A1 | 12/1998 |
| FR | 2679252      | 1/1993  |
| JP | A 6-90757    | 4/1994  |
| JP | A 8-308596   | 11/1996 |
| WO | WO 92/08117  | 5/1992  |
| WO | WO 97/20070  | 6/1997  |
| WO | WO 97/46700  | 12/1997 |
| WO | WO 98/35059  | 8/1998  |
| WO | WO 99/07883  | 2/1999  |
| WO | WO 99/19509  | 4/1999  |

OTHER PUBLICATIONS

Begovich et al. A specific HLA-DP beta allel is associated with pauciarticular juvenile rheumatoid arthritis but not adult rheumatoid arthritis. PNAS, vol. 86, pp. 9489-9493, Dec. 1989.*
Scharf et al. Specific HLA-DQB and HLA-DRB1 alleles confer susceptibility to pemphigus vulgaris. PNAS, vol. 86, pp. 6215-6219, Aug. 1989.*
Evans, et al. The Genotype Distribution of Shared-epitope DRB1 alleles suggest a recessive mode of inheritance of the rheumatoid arthritis disease-susceptibility gene. Arthritis and Rheumatism. vol. 38, pp. 1754-1761, 1995.*
Kawai et al. A simple method of HLA-DRB typing using enzymatically amplified DNA and immobilized probes on microtiter plate. Human Immunology, vol. 41, pp. 121-126, 1991.*
Weyand et al. Correlation betwen Disease pphenotype and genetic heterogeneity in Rheumatoid Arthritis. The Journal of Clinical Investigation, Inc. vol. 95, vol. 2120-2126, May 1995.*
Garcia-Pacheco et al. "Routine HLA DRB/DQB oligonucleotide typing by a non-radioactive dot-blot micromethod", Journal of Immunological Methods 180 (1995) 35-43.
Bein et al., "Rapid HLA-DRB1 genotyping by nested PCR amplification", Tissue Antigens 1992: 39: 68-73, XP-000949259.
Kim et al., "Predominance of HLA-DRB1*0405 in Korean patients with rheumatoid arthritis", Annals of the Rheumatic Diseases 1995; 54: 988-990, XP-000878854.
Kawai et al., A Simple Method of HLA-DRB Typing Using Enzymatically Amplified DNA and Immobilized Probes on Microtiter Plate, Human Immunology 41, 121-126 (1994), XP-000890112.

(Continued)

Primary Examiner—Kenneth R. Horlick
(74) Attorney, Agent, or Firm—Oliff & Berridge, PLC

(57) ABSTRACT

A patient's genetic predisposition to a disease may be analyzed by placing, in the presence of probes, at least one type of amplicon, derived from the amplification of at least one polymorphic region of nucleic acid from the patient. The polymorphic region is a polymorphic region of interest with respect to the disease(s) being sought. The probes include at least one specific "low-resolution" typing probe that has the ability to hybridize to the polymorphic region of interest of at least one gene or a group of alleles of this gene carried by the amplicon and associated with the disease(s); and at least one specific "high-resolution" subtyping probe that has the ability to hybridize to the polymorphic region of interest of the allele or of the group of alleles specific for the "low-resolution" typing probe, the high-resolution probe(s) making it possible to distinguish the allele(s) associated with susceptibility and/or the allele(s) associated with resistance to the disease(s), according to whether or not they hybridize.

21 Claims, No Drawings

OTHER PUBLICATIONS

Evans et al., "The Genotypic Distribution of Shared-Epitope DRB1 Alleles Suggests A Recessive Mode of Inheritance Of The Rheumatoid Arthritis Disease-Susceptibility Gene", Arthritis & Rhuematism, vol. 38, No. 12, Dec. 1995, pp. 1754-1761, XP-000878857.

XP-002133035, Derwent Publications Ltd., "Detection and typing of class I MHC HLA-DR antigens—can check multiple specimens easily and type all HLA-DR (D-related) antigens known to be present in the Japanese population".

Allen et al. "Allele-Specific HLA-DRB1 Amplification of Forensic Evidence Samples with Mixed Genotypes", BioTechniques, vol. 19, No. 3 (1995), XP-002133033.

XP-002133036, Derwent Publications Ltd., "Oligo:nucleotide probes for HLA-DR typing of human DNA—and reagent kits containing probes, new amplification primers and buffers".

Petersdorf et al., "Polymorphism of HLA-DRw52-associated DRB1 genes as defined by sequence-specific oligonucleotide probe hybridization and sequencing", Tissue Antigens, vol. 38, No. 4, Oct. 1, 1991, pp. 169-177, XP000673021.

Haworth et al., Polymyalgia Rheumatica Is Associated With Both HLA-DRB1*0401 and DRB1*0404, British Journal of Rheumatology 1996; 35:632-635, XP-000878853.

Takeuchi et al., "Positive and negative association of HLA-DR genotypes with Japanese rheumatoid arthritis", Clinical and Experimental Rheumatology 14: 17-22, 1996., XP-000878869.

Nepom et al., "HLA Genes Associated With Rheumatoid Arthritis" Arthritis and Rheumatism, vol. 32, No. 1 (Jan. 1989), XP-000879219.

Wagner et al., "HLA Markers And Prediction Of Clinical Course And Outcome In Rheumatoid Arthritis", Arthritis & Rheumatism, vol. 40, No. 2. Feb. 1997, pp. 341-351, XP-000878856.

Gao et al., DNA Typing for Class II HLA Antigens with Allele-Specific of Group-Specific Amplification, Human Immunology, vol. 30, 1991, pp. 147-154, XP-000889911.

Cereb et al., "Locus-specific amplification of HLA class I from genomic DNA: locus-specific sequences in the first and third introns of HLA-A, -B, and -C alleles", Tissue Antigens, vol. 45, 1995, pp. 1-11, XP-000197333.

Angelini et al. "High-resolution analysis of the human HLA-DR polymorphism by hybridization with sequence-specific oligonucleotide probes", Proceedings of the National Academy of Sciences, vol. 83, 1986, pp. 4489-4493, XP-002133034.

Wordsworth et al., "HLA-DR typing using DNA amplification by the polymerase chain reaction and sequential hybridization of sequence-specific oligonucleotide probes", Immunogenetics, vol. 32, Jan. 1, 1990, pp. 413-418, XP-002911048.

Nepom et al., "MHC Class-II Molecules And Autoimmunity", Annu. Rev. Immunol. 1991. 9:493-525.

Weiss et al., "Organization, Sequence and Expression of the HLA-B27 Gene: A Molecular Approach to Analyze HLA and Disease Associations", Immunobiol., vol. 170, pp. 367-380 (1985).

Lawrence, "Rheumatoid Arthritis—Nature or Nurture?", Ann. Rheum. Dis. (1970), 29, 357.

Stastny et al. "HLA-DR4 And Other Genetic Markers In Rheumatoid Arthritis", British Journal of Rheumatology, 1988; 27 (suppl II): 132-138.

Baarsma "The epidemiology and genetics of endogenous uveitis: a review", Current Eye Research, vol. 11, supplement 1992, 1-9.

Stastny et al. "The Human Immune Response Region (HLA-D) and Disease Susceptibility", Immunological Rev. (1983), vol. 70.

Benjamin et al., "Guilt by association: HLA-B27 and ankylosing spondylitis" Immunology Today, vol. 11, No. 4 1990.

The Lancet, Apr. 28, 1979, pp. 921-922.

Todd et al., "A Molecular Basis for MHC Class II-Associated Autoimmunity", Science, vol. 240.

Wordsworth et al., "HLA-DR4 subtype frequencies in rheumatoid arthritis indicate that DRB1 is the major susceptibility locus within the HLA class II region", Proc. Natl. Acad. Sci, vol. 86, 99. 10049-10053, Dec. 1989, Immunology.

Gregersen et al., "Molecular diversity of HLA-DR4 haplotypes", Proc. Natl. Acad. Sci., vol. 83, pp. 2642-2646, Apr. 1986, Immunology.

Hiraiwa et al., "Structural requirements for recognition of the HLA-Dw14 class II epitope: A key HLA determinant associated with rheumatoid arthritis", Proc. Natl. Acad. Sci, vol. 87, pp. 8051-8055, Oct. 1990, Immunology.

Hill et al., "HLA class 1 typing by PCR: HLA-B27 and an African B27 subtype", The Lancet, vol. 337; Mar. 16, 1991.

The Lancet, Apr. 28, 1973, pp. 904-9073.

Schlosstein et al., "High Association Of An HL-A Antigen, W27, With Ankylosing Spondylitis", The New England Journal of Medicine, Apr. 5, 1973.

Stastny, "Association Of The B-Cell Alloantigen DRw4 With Rheumatoid Arthritis", The New England Journal of Medicine, vol. 298, No. 16.

Nepom et al., "HLA Genes Associated with Rheumatoid Arthritis", Arthritis and Rheumatism, vol. 32, No. 1 (Jan. 1989).

Gregersen et al., "The Shared Epitope Hypothesis", Arthritis and Rheumatism, vol. 30, No. 11 (Nov. 1987).

Kirveskari et al., "False-Negative Serological HLA-B27 Typing Results May Be Due To Altered Antigenic Epitopes and Can Be Detected By Polymerase Chain Reaction", British Journal of Rheumatology, 1997;36:185-189.

Neumuller et al., "Failure of the serological determination of HLA-B27 due to antigen masking in patients with ankylosing spondylitis", Rheumatol Int. (1993) 13: 163-167.

Gu et al., "Inducible functions in hybrids of a Lyt-2$^+$ BW5147 transfectant and the 2C CTL line", Immunogentics, 36: 283-293, 1992.

P. Guerne et al., "Molecular Analysis of HLA-DR Polymorphism in Polymyalgia Rheumatica", *The Journal of Rheumatology*, 1997, 24:4, pp. 671-675.

B. Frankenberger et al., "Routine Molecular Genotyping of HLA-B27 in Spondyloarthropathies Overcomes the Obstacles of Serological Typing and Reveals an Increased B*2702 Frequency in Ankylosing Spondylitis", *The Journal of Rheumatology*, 1997,:24:5, pp. 899-903.

I. Buyse et al., "Rapid DNA Typing of Class II HLA Antigens Using the Polymerase Chain Reaction and Reverse Dot Blot Hybridization", pp. 1-14.

J.-M. Tiercy et al., "A New Approach for the Analysis of HLA Class II Polymorphism: 'HLA Oligotyping'", *Blood Reviews*, 1990, 4 pp. 9-15.

L. Jianhao et al., " Ankylosing Spondylitis and Heterogeneity of HLA-B27 in Chinese", *Chinese Medical Journal*, 109(4), 1996, pp. 313-316.

I. Auger et al., "HLA-DR and the Development of Rheumatoid Arthritis", *Autoimmunity*, vol. 26, pp. 123-128.

R. W. Vaughan et al., "The Application of Oligonucleotide Probes to HLA Class II Typing of the DRB Sub-region", *Tissue Antigens*, 1990: 36: pp. 149-155.

B. P. Wordsworth et al., "HLA-DR Typing Using DNA Amplification by the Polymerase Chain Reaction and Sequential Hybridization to Sequence-Specific Oligonucleotide Probes", *Immunogenetics*, 1990, 32: pp. 413-418.

I. E. Van Der Horst-Bruinsma et al., "Influence of Non-inherited Maternal HLA-DR Antigens on Susceptibility to Rheumatoid Arthritis", *Ann Rhum Dis*, 1 198; 57, pp. 672-675.

A. Hill et al., "HLA Class I Typing by PCR: HLA-B27 and An African B27 Subtype", *The LANCET*, vol. 337, Mar. 16, 1991, pp. 640-642.

U. Varshney et al., "Inosine Incorporation in GC Rich RNA Probes Increases Hybridization Sequence Specificity", *Nucleic Acids Research*, vol. 16, No. 9, 1988, p. 4162.

G. H. Fallet et al., "Coexisting Rheumatoid Arthritis and Ankylosing Spondylitis", *The Journal of Rheumatology*, 14:6, 1987, pp. 1135-1138.

S. Kawai et al., "Routine Low and High Resolution Typing of The HLA-DRB Gene Using The PCR-MPH (Microtitre Plate Hybridization) Method", *European Journal of Immunogenetics*, 1996, 23, pp. 471-486.

H. Kim et al., "Predominance of HLA-DRB1*0405 in Korean Patients with Rheumatoid Arthritis", *Annals of the Rheumatic Diseases*, 1995, 54: pp. 988-990.

C. G. Meyer et al., "HLA-D Alleles Associated with Generalized Disease, Localized Disease, and Putative Immunity in *Onchocerca volvulus* Infection", *Proc. Natl. Acad. Sci. USA*, vol. 91, Aug. 1994, pp. 7515-7519.

R. Helmuth et al., "HLA-DQα Allele ad Genotype Frequencies in Various Human Populations, Determined by Using Enzymatic Amplification and Oligonucleotide Probes", *Am. J. Hum. Genet.*, 1990, 47, pp. 515-523.

H. Kang et al., "Comparison of HLA Class II Genes in Caucasoid, Chinese, and Japanese Patients with Primary Sjögren's Syndrome", *The Journal of Immunology*, vol. 150, No. 8, Apr. 15, 1993, pp. 3615-3623.

T. Evans et al., "The Genotypic Distribution of Shared-Epitope DRB1 Alleles Suggests A Recessive Mode of Inheritance of the Rheumatoid Arthritis Disease-Susceptibility Gene", *Arthritis & Rheumatism*, vol. 38, No. 12, Dec. 1995, pp. 1754-1761.

J. A. Noble et al., "The Role of HLA Class II Genes in Insulin-Dependent Diabetes Mellitus: Molecular Analysis of 180 Caucasian, Multiplex Families", *Am. J. Hum.*, 59, 1996, pp. 1134-1148.

S. J. Scharf et al., "Rapid Typing of DNA Sequence Polymorphism at the HLA-DRB1 Locus Using the Polymerase Chain Reaction and Nonradioactive Oligonucleotide Probes", *Human Immunology*, 30, 1991, pp. 190-201.

O. Dominguez et al., "Molecular Typing of HLA-B27 Alleles", *Immunogenetics*, 36, 1992, pp. 277-282.

Applied Biosystems pp. 1-144, 2005.

* cited by examiner

METHOD FOR ANALYZING A PATIENT'S GENETIC PREDIPOSITION TO AT LEAST ONE DISEASE AND AMPLIFICATION ADAPTED TO SUCH A METHOD

The present invention relates to a method for analyzing a patient's genetic predisposition to at least one disease, such as rheumatoid arthritis or ankylosing spondylitis.

Each individual has his or her own genetic inheritance, inherited from his or her ascendants. This particular genetic context can sometimes actively contribute to the appearance and/or development of certain conditions: infections with a pathogenic agent (AIDS virus for example), autoimmune diseases (rheumatic diseases for example). The genes of the Major Histocompatibility Complex (MHC), in particular the genes encoding the HLA antigens (human leukocyte antigens), play a predominant role in the development of articular autoimmune pathologies such as rheumatoid arthritis (Lawrence, 1970; Stastny, 1978; Khan, 1979; Stastny, 1983; Gregersen, 1986; Gregersen, 1987; Stastny, 1988; Todd, 1988; Wordsworth, 1989; Nepom, 1989; Hiraiwa, 1990; Nepom, 1991) or ankylosing spondylitis (Brewerton, 1973; Schlosstein, 1973; Benjamin, 1990).

It has been possible to associate a considerable part of the genetic component of susceptibility to rheumatoid arthritis with the HLA-DRB genes, which encode the β chain of the HLA-DR molecules involved in the presentation of peptides to T lymphocytes, a pivotal function at the center of the mechanisms regulating the immune response. More precisely, it has been shown that the presence of a particular sequence of five amino acids, corresponding to positions 70 to 74 of the third hypervariable region of HLA-DRβ1 molecules, is found for various alleles reported to be associated with rheumatoid arthritis. The involvement of this "shared epitope" corresponding to the sequences QKRAA (SEQ ID NO: 28) or QRRAA (SEQ ID NO: 29) or RRRAA (SEQ ID NO: 30) (one-letter amino acid code) is nowadays well documented. This molecular explanation is also coherent with the observation of progressive severity of the disease when the genotype comprises none, one or two susceptibility alleles, commonly termed dose-effect.

Ankylosing spondylitis is another inflammatory disease for which a very strong association with the HLA-B27 antigen (relative risk: 69.1) is observed (Baarsma, 1992). In 1977, Schlosstein published the strong association between HLA-B27 and various spondylarthropathies (Schlosstein, 1977). Various hypotheses have been put forward, again involving the function of presentation of specific peptides, in order to explain this association of HLA-B27 molecules.

A positive association has also been published between HLA-B27 and acute anterior uveitis (relative risk: 8.2).

The detection of HLA-B27 antigen(s) has a definite clinical value, as witnessed by the fact that this is a commonly carried out analysis recommended in the course of a rheumatology consultation.

The detection of one or more HLA-B*27 allele(s) is also possible using the molecular biology techniques of amplification and of analysis of the specific regions of interest.

Thus, in 1985, Weiss published the organization, sequence and expression of the HLA-B27 gene. In 1991, Hill published a technique for amplifying by PCR the polymorphic regions of the HLA-B gene and the detection of HLA-B*2703 by hybridization with a specific probe (Hill, 1991). In 1992, Dominguez published the description of the first method for genotyping B27, after PCR amplification of the polymorphic regions of the HLA-B gene.

Currently, with regard to rheumatoid arthritis, the identification of one or more susceptibility allele(s) is generally carried out routinely in the course of low resolution or generic HLA-DR typing, enabling in particular the detection of one or more HLA-DR4 antigen(s) or one or more HLA-DRB1*gr04 allele(s).

These tests are carried out by centers which specialize in the study of HLA genes, such as blood transfusion centers or certain specialized hospitals. This identification therefore requires the sending of a sample and the use of fairly laborious technology. There are therefore many negative consequences, such as:

the risks of losing the sample, the considerable amount of time taken for this identification, the relatively high cost of said identification, and the lack of control of the party requesting the service over the provider of the service.

The state of the art is very limited with regard to HLA-DR and rheumatoid arthritis associations, which use molecular biology technology.

In the context of ankylosing spondylitis, the state of the art consists essentially of immunology techniques. This is the case of patent application WO-A-95/30152, which allows the identification of the B27 antigen. Thus, with regard to ankylosing spondylitis, a simple search for the HLA-B27 antigen is conventionally carried out using a serological technique (flow cytometry or cytotoxicity, with a specific anti-B27 antibody).

These techniques are rapid, but false-negative reactions are sometimes observed due to masking of the B27 antigens by autoantibodies or peptides (Neumüller, 1993; Kirveskari, 1997). In addition, as with any technique for analyzing antigens expressed at the surface of lymphocytes, precautions for good conservation of the cells are necessary, and sometimes restrictive.

Still in this field, the state of the art also consists of molecular biology techniques. Thus, patent U.S. Pat. No. 4,971,902 relates to probes for diagnosing a patient's predisposition to rheumatoid arthritis. These probes are based on recognition of the DRB1*gr04 group of alleles.

However, while this DRB1*gr04 group of alleles is effectively associated with rheumatoid arthritis, not all the alleles currently known (DRB1*gr0401 to DRB1*gr0427) are necessarily associated with this disease. The result of this may be that, if typing is limited to the DRB1*gr04 group of alleles, then depending on the alleles present, false positives which will unnecessarily alarm the physician and the patient may, besides true positives or true negatives, be obtained.

Whether a serological technique (analysis of DR antigens using a battery of sera of known specificity: results given according to the nomenclature DR1 to DR10) or a molecular biology technique (analysis of DRB1 alleles: results given according to the nomenclature DRB1*01 to DRB1*10) is used, the clinician is essentially interested in the presence of one or more DR4 antigen(s) or one or more DRB1*gr04 allele(s), possibly with the "dose-effect" information.

In the event of results suggesting a predisposition to the disease, a second test is generally carried out, using a "DR4 subtyping" "high-resolution" molecular biology technique, in order to specify the DRB1*gr04 allele (DRB1*gr0401 to gr0427 according to the official nomenclature in 1998), only the DRB1*gr0401, gr0404, gr0405 and gr0408 alleles being reported to be associated with the disease.

These tests are reliable but long, taking several days, and expensive.

The analytical method claimed allows an analysis which is simplified from a practical point of view, more rapid, taking less than two hours, after preparation of the amplicons, and relatively inexpensive.

To this effect, the present invention relates to a method for analyzing a patient's genetic predisposition to at least one disease, consisting in placing a liquid sample containing at least one type of amplicon, derived from the amplification of at least one polymorphic region of interest with respect to the disease(s) being sought, in the presence of probes chosen in the following way:

at least one specific "low-resolution" typing probe capable of hybridizing on the polymorphic region of interest of at least one gene or a group of alleles of this gene carried by the amplicon and associated with said disease(s), and at least one specific "high-resolution" subtyping probe capable of hybridizing on said polymorphic region of interest of the allele or of the group of alleles specific for the "low-resolution" typing probe, the high-resolution probe(s) making it possible to distinguish the allele(s) associated with susceptibility, and/or the allele(s) associated with resistance, to said disease(s), according to whether or not they hybridize.

In order to detect the presence of another allele, when a single allele of the gene or of the group of alleles of this gene has been detected, with at least one specific low-resolution typing probe, corresponding to the other group(s) of alleles, the method consists in placing the amplicons in the presence of at least one probe specific for at least one other allele, corresponding to the polymorphism of said gene or of said group of alleles of this gene detected by the low-resolution probe(s).

Each low- or high-resolution probe specific for the disease (s) being sought comprises at least one motif characteristic of said disease(s) being sought.

When the desire is to detect HLA-DR alleles for genetic susceptibility to rheumatoid arthritis and other associated diseases, use is made of:

at least one low-resolution probe capable of hybridizing on the DRB1*gr04 group of alleles, at least one high-resolution probe associated with genetic susceptibility to rheumatoid arthritis, capable of hybridizing with the following alleles: DRB1*0101, DRB1*gr0401, DRB1*gr0404, DRB1*gr0405, DRB1*gr0408 and DRB1*gr1402, at least one high-resolution probe associated with genetic resistance to rheumatoid arthritis, capable of hybridizing with the following alleles: DRB1*gr0402, DRB1*gr0403, DRB1*gr0406 and DRB1*gr0407.

In addition, use is made of at least one low-resolution probe capable of hybridizing on the DRB1*01 group of alleles and on the DRB1*10 allele.

When the desire is to detect the presence of another allele, when a single allele of the DRB1*gr04 group of alleles has been detected, use is made of at least one probe capable of hybridizing on the following alleles: DRB1*02, DRB1*03, DRB1*07, DRB1*08, DRB1*09, DRB1*11, DRB1*12, DRB1*13 and DRB1*14.

With regard to the probes relating to these alleles, use is made of:

a SEQ ID NO: 3 probe, for the DRB1*gr04 typing, two high-resolution probes associated with genetic susceptibility to rheumatoid arthritis:

SEQ ID NO: 4 for DRB1*gr0401,

SEQ ID NO: 7 for DRB1*0101, DRB1*gr0404, DRB1*gr0405, DRB1*gr0408 and DRB1*1402, two high-resolution probes associated with genetic resistance to rheumatoid arthritis:

SEQ ID NO: 5 for DRB1*gr0402, and

SEQ ID NO: 6 for DRB1*gr0403, DRB1*gr0406 and DRB1*gr0407.

More precisely, use is also made of a high-resolution probe, SEQ ID NO: 8, specific for DRB1*gr0405 and associated with genetic susceptibility to rheumatoid arthritis.

In addition, the following two probes are used for the typing:

SEQ ID NO: 11 for the DRB1*01 group of alleles, and

SEQ ID NO: 15 for the DRB1*10 allele.

When the desire is to detect the presence of another allele, when a single allele of the DRB1*gr04 group of alleles has been detected, use is made of the following four typing probes:

SEQ ID NO: 13 for DRB1*02,

SEQ ID NO: 14 for DRB1*07 and DRB1*09,

SEQ ID NO: 16 for DRB1*08 and DRB1*12, and

SEQ ID NO: 12 for DRB1*03, DRB1*11, DRB1*13 and DRB1*14.

In any event, each low- or high-resolution probe specific for the alleles for genetic susceptibility to rheumatoid arthritis and other associated diseases comprises one of the following characteristic motifs: QKRAA (SEQ ID NO: 28), QRRAA (SEQ ID NO: 29) or RRRAA (SEQ ID NO: 30).

At least one control probe capable of hybridizing with the set of DRB1 genes is used to allow detection of all the DRB1 genes, such as SEQ ID NO: 1: TTC GAC AGC GAC GTG GGG.

If the intention is also to detect alleles for genetic susceptibility to ankylosing spondylitis and other associated diseases, use is made of at least one low-resolution probe, such as SEQ ID NO: 10, capable of hybridizing on the HLA-B gene and specific for the HLA-B27 group of alleles.

If the intention is also to detect genetic susceptibility associated with lupus erythematosus disseminatus, with collagen disease, with Sjögren's syndrome and other associated diseases, use is made of at least one low-resolution probe, such as SEQ ID NO: 19, capable of hybridizing on the HLA-DR gene and specific for the HLA-DRB1*03 group of alleles.

Whatever the detection sought, a maximum of 38.89% of the bases of the same low-resolution or high-resolution probe are replaced with at least one analogous base, such as inosine.

According to one variant of implementation of the method, each specific low-resolution or high-resolution probe is placed in a well of a microtitration plate, independently of the other probes.

According to another variant of implementation of the method, all the reactions are carried out simultaneously.

Prior to the method stated above, at least one amplification of the polymorphic regions(s) of interest is carried out.

Amplification of the polymorphic region(s) of interest associated with HLA-DR and amplification of the polymorphic region(s) of interest associated with HLA-B are carried out simultaneously.

According to one variant of implementation, a second amplification of at least one region is carried out, which is more highly targeted than that already carried out on the polymorphic region, this more highly targeted region being a region of interest with respect to the disease(s) being sought, and the amplicons obtained are placed in the presence of the previously defined probes.

According to this variant, the first amplification is carried out at the same time as, or prior to, the second, more highly targeted amplification.

The present invention also relates to amplification of a sequence corresponding to the DRB1*gr04 groups of alleles, with a view to using it in a method for analyzing a patient's genetic predisposition to rheumatoid arthritis, which consists in using SEQ ID NO: 20 primers in combination with SEQ ID NO: 21 primers.

The present invention also relates to amplification of a sequence corresponding to the B27 allele, with a view to using it in a method for analyzing a patient's genetic predisposition to ankylosing spondylitis, which consists in using SEQ ID NO: 22, SEQ ID NO: 23 and/or SEQ ID NO: 25 primers in combination with SEQ ID NO: 24 and/or SEQ ID NO: 26 primers.

In addition, the invention may consist in combining the two amplifications described in the two paragraphs above, with a view to using them in a method for analyzing a patient's genetic predisposition to rheumatoid arthritis and/ or to ankylosing spondylitis.

In this case, the amplification, in which the final concentration of primers for amplifying the sequence corresponding to the DRB1*gr04 groups of alleles is higher than the final concentration of primers for amplifying the sequence corresponding to the B27 alleles.

In one variant of implementation, the above amplification is combined with the amplification of a sequence corresponding to a more highly targeted region included in the DRB1*gr04 allele, which consists in using SEQ ID NO: 21 primers in combination with SEQ ID NO: 27 primers.

The attached examples are given by way of explanatory example and are in no way limiting in nature. They will make it possible to understand the invention more clearly.

The present invention relates to a method for detecting genetic diseases which is rapid and inexpensive. This novel technology may be used with all genetic diseases and particularly with rheumatoid arthritis, ankylosing spondylitis and other autoimmune diseases, such as collagen diseases (lupus, scleroderma, etc.), also encountered during a rheumatology consultation.

It is a method dedicated to analyzing an individual's genetic predispositions to certain diseases, using a molecular biology technique which allows the simultaneous analysis of several genes. This method may be advantageously applied to the analysis of an individual's genetic predispositions for a disease, or a set of related diseases, associated with one or more genes. This method may be applied to the analysis of an individual's genetic predispositions to certain inflammatory autoimmune diseases, such as rheumatoid arthritis and ankylosing spondylitis.

The advantage of this method is obtaining, in one step, with a multiple but single test, a complete set of relevant information of clinical interest (diagnostic interest, prognostic interest and interest in terms of therapeutic direction). The method can be broken down into several steps:

1) extraction of nucleic acids from a biological sample from the individual, 2) amplification of the regions of interest for which a polymorphism associated with a genetic predisposition to a pathological condition has been described, and 3) simultaneous analysis of the amplicons using a set of hybridization reactions implementing a set of molecular probes which allow the precise analysis of given alleles or groups of alleles.

I—EXAMPLE OF SIMULTANEOUS ANALYSIS OF AN INDIVIDUAL'S GENETIC PREDISPOSITIONS FOR RHEUMATOID ARTHRITIS AND ANKYLOSING SPONDYLITIS

1°) Extraction of Deoxyribonucleic Acids (DNAs) from a Peripheral Blood Sample:

This extraction is carried out entirely conventionally. In fact, it is possible to use any DNA extraction technique which makes it possible to obtain material which can subsequently be amplified using an amplification method such as the Polymerase Chain Reaction (PCR). These cell lysis techniques, with extraction and then purification of the nucleic acids, are conventionally those recommended for genetic analyses, or rapid techniques using commercial products, such as QIAmp Blood Kit (trademark) from QIAGEN S.A.

2°) Simultaneous Amplification by PCR:

This amplification concerns the following loci the HLA-DR locus: including the region of exon 2 corresponding to codons 5 to 94, according to the official nomenclature, of the HLA-DRB genes the HLA-B locus: including the region of exon 2 corresponding to codons 25 to 114, according to the official nomenclature, of the HLA-B gene.

Table 1 below describes the primers used during the amplification of the two loci described above. It also gives the set of physicochemical conditions for carrying out this amplification.

TABLE 1

Simultaneous amplification of the regions of interest HLA-DR and HLA-B

| | |
|---|---|
| Primers | P1 (5' primer-DR): SEQ ID NO: 20 |
| | CCG GAT CCT TCG TGT CCC CAC AGC ACG |
| | (5' > 3') |
| | P2 (3' primer-DR): SEQ ID NO: 21 |
| | TCG CCG CTG CAC TGT GAA G (5' > 3') |
| | P3 (5' primer-B): SEQ ID NO: 22 or |
| | SEQ ID NO: 23 |
| | GGG AGG AGC GAG GGG ACC CCA G (5' > 3') or |
| | GGG AGG AGC GAG GGG ACC GCA G (5' > 3') |
| | P4 (3' primer-B): SEQ ID NO: 24 |
| | ATC TCG GAG CCG GAG ACT (5' > 3') |
| Reaction mixture | 10X TEMAG buffer (*): 10 µl |
| | dNTPs (20 mM): 1 µl (0.2 mM final) |
| | P1 (30 µM): 0.8 µl (0.25 µM final) |
| | P2 (30 µM): 0.8 µl (0.25 µM final) |
| | P3 (30 µM): 1.3 µl (0.4 µM final) |
| | P4 (30 µM): 1.3 µl (0.4 µM final) |
| | AmpliTaq (5 U/µl): 0.5 µl (2.5 U) |
| | DNA: 100–500 ng |
| | H$_2$O: QS for 100 µl |
| Amplification program | (5 min at 96° C.) + 10 × (10 sec at 98° C. + 30 sec at 65° C. + 30 sec at 72° C.) + 30 × (20 sec at 96° C. + 30 sec at 65° C. + 30 sec at 72° C.) |

(*): 10X TEMAG buffer: 500 mM Tris-HCl, pH 8.8, 150 mM ammonium sulfate, 15 mM MgCl$_2$, 500 µM EDTA and 0.1% gelatin.

3°) Simultaneous Analysis of the Amplicons:

This analysis uses a set of hybridization reactions implementing a set of oligonucleotide probes which allow the precise analysis of HLA-DRB1 and HLA-B*27 alleles or groups of alleles which are important for studying genetic predisposition to rheumatoid arthritis and to ankylosing spondylitis, in particular.

Table 2 describes the set of probes which is used for detecting these two diseases. The indications given, from left to right, are as follows:

- the probe reference assigned in HLA nomenclature,
- the sequence number assigned in this document,
- the HLA gene concerned,
- the sequence making up this probe, and
- the location of the codons (three nucleotides) on the HLA genes.

TABLE 2

Oligonucleotide probes

| Probe | SEQ ID NO | HLA Gene | Sequence (5' > 3') | Location (codons) |
|---|---|---|---|---|
| C+ | 1 | DR | TTC GAC AGC GAC GTG GGG | 40–45 |
| C– | 2 | — | TAT GAA ACT TAT GGG GAT AC | |
| 4 | 3 | DR | GAT ACT TCT ATC ACC A | 29–34 |
| QK71 | 4 | DR | GAG CAG AAI CGG ICC | 69–73 |
| | | | GAG CAG AAG CGG GCC | |
| IDE71 | 5 | DR | CTG GAA GAC GAI CGG | 68–72 |
| | | | CTG GAA GAC GAG CGG | |
| E74 | 6 | DR | AGC AIA IGC IGG ICI AII | 69–75 |
| | | | AGC AGA GGC GGG CCG AGG | |
| QR71 | 7 | DR | CAG AGG CGI GII ICI GTG | 70–75 |
| | | | CAG AGG CGG GCC GCG GTG | |
| S57 | 8 | DR | GCC TAG CGC CGA GTA | 55–60 |
| C + (B) | 9 | B | AAA TAC CTC ATG GAG TGG GAG CC | 25–32 (*) |
| B27 | 10 | B | TGC CTT IGC CTT ICA GAT | 90–95 (*) |
| | | | TGC CTT GGC CTT GCA GAT | |
| 1 | 11 | DR | TGG CAG CTT AAG TTT GAA | 9–14 |
| 52 | 12 | DR | TAC TCT ACG TCT GAG T | 10–15 |
| 2 | 13 | DR | CAG CCT AAG AGG GAG TG | 10–15 |
| 7 + 9 | 14 | DR | IAG GTI GAC AIC GTG TGC | 74–79 |
| | | | CAG GTG GAC ACC GTG TGC | |
| 10 | 15 | DR | GGA GGA GGT TAA GTT | 8–13 |
| 8 + 12 | 16 | DR | CTC TAC GGG IGA GT | 10–15 |
| | | | CTC TAC GGG TGA GT | |
| 3 | 19 | DR | CCG GGT GGA CAA CIA C | 73–78 |
| | | | CCG GGT GGA CAA CTA C | |
| D1 | 17 | DR | GAA CAG CCA GAA GGA C | 61–66 |
| D6 | 18 | B | CTC GCT CTG GTT GTA GTA G | 106–113 (*) |

(*) probe corresponding to the noncoding complementary strand

For certain probes, a second sequence in italic characters specifies the natural sequence, i.e. the sequence consisting only of the four nucleotides adenosine (A), thymine (T), guanine (G) and cytosine (C). The other sequences repeat the same nucleotides with the exception of the substitution of some with different nucleotides. In the present case, this is inosine.

Certain sequences do not contain any inosine, this is the case of SEQ ID NOs: 1, 2, 3, 8, 9, 11, 12, 13, 15, 17 and 18. Others contain few inosines, this is the case of SEQ ID NO: 19, in which there is one inosine out of a total of sixteen nucleotides, i.e. 6.25% difference relative to the basic sequence. Others contain many more inosines, such as for SEQ ID NO: 6, in which there are seven inosines out of a total of eighteen nucleotides, i.e. approximately 38.89% difference relative to the basic sequence.

The use of inosines makes it possible to further improve the specificity of the probes with respect to the sequences to which they will hybridize. The specificity of the capture probes is clearly specified in Table 3 below.

TABLE 3

Main specificities of the capture probes

| Probe | SEQ ID NO | Specificity |
|---|---|---|
| C+ | 1 | All DRB1* |
| C– | 2 | None |
| 4 | 3 | DRB1*gr04 |
| QK71 | 4 | DRB1*gr0401 in particular, allele containing the motif QKRAA (SEQ ID NO: 28) corresponding to the shared epitope |

TABLE 3-continued

Main specificities of the capture probes

| Probe | SEQ ID NO | Specificity |
|---|---|---|
| IDE71 | 5 | DRB1*gr0402 in particular |
| E74 | 6 | DRB1*gr0403, gr0406 and gr0407 in particular |
| QR71 | 7 | DRB1*0101, gr0404, gr0405, gr0408 and 1402 in particular, allele containing the motif QRRAA (SEQ ID NO: 29) corresponding to the shared epitope |
| S57 | 8 | DRB1*gr0405 in particular |
| C + (B) | 9 | All B* |
| B27 | 10 | B*27 in particular |
| 1 | 11 | DRB1*01 |
| 52 | 12 | DREl*03, 11, 13 and 14 in particular |
| 2 | 13 | DRB1*02 |
| 7 + 9 | 14 | DRB1*07 and 09 |
| 10 | 15 | DRB1*10 |
| 3 | 19 | DRB1*03 in particular |
| 8 + 12 | 16 | DRB1*08 and 12 in particular |

In this Table 3, the term "in particular" is sometimes associated with certain alleles. The explanation lies in the fact that other alleles exist. Thus, with SEQ ID NO: 5, DRB1*gr0402 is detected, but also DRB1*gr0414. The latter is very rare, so rare that, to date, no study has been undertaken to link its presence to that of rheumatoid arthritis. However, since the motifs of these two alleles are similar within the polymorphic regions of interest, there is a strong chance that their susceptibility to this disease is identical.

Probes D1 and D6, corresponding to SEQ ID NOs: 17 and 18, are detection probes.

They recognize the regions observed in all the alleles of the same gene. Thus, the SEQ ID NO: 17 probe is chosen in a conserved region of the HLA DR gene, while the SEQ ID NO: 18 probe is chosen in a conserved region of the HLA B gene.

This probe analysis may be carried out on microtitration plates or microplates, the format of which is standardized. These plates comprise individual strips of eight wells, which can be assembled depending on the number of tests to be carried out. Due to the demands of convenience and cost, the use of two strips per test is advantageous.

The objective is to obtain results with a minimum of strips, since the production cost must be as low as possible, while at the same time having a very high level of performance. This minimum corresponds to two strips.

In the case of rheumatoid arthritis and of ankylosing spondylitis, two strips may therefore be used, which will be named R1 and R2, respectively. While one possibility is provided for strip R1, two scenarios are possible with regard to R2.

disposition to rheumatoid arthritis. More particularly, the SEQ ID NOs: 4 and 7 probes make it possible to detect the alleles associated with susceptibility to rheumatoid arthritis, and the SEQ ID NOs: 5 and 6 probes make it possible to detect the alleles associated with resistance to said rheumatoid arthritis. The SEQ ID NO: 8 probe makes it possible to confirm the presence of a DRB1*gr0405 allele.

Strip R2 comprises a positive control (SEQ ID NO: 9) which makes it possible to detect the amplicons corresponding to exon 2 of the HLA-B gene, which makes it possible to verify that the region of interest between the primers P3 and P4 described in Table 1 was indeed that amplified.

It comprises, firstly, a SEQ ID NO: 10, which makes it possible to detect the B*27 group of alleles, and which is used to determine whether an individual is predisposed to developing ankylosing spondylitis.

The remainder of this strip consists of low-resolution probes, namely SEQ ID NOs: 11 to 16, which make it possible to complete the analysis of the two haplotypes of any individual, in particular indicating whether the presence of alleles for susceptibility or for resistance to rheumatoid arthritis, revealed with strip R1, relates to one or to both haplotypes (dose-effect).

Depending on the balance between susceptibility allele, resistance allele and neutral allele, the risks of developing more or less severe rheumatoid arthritis are different and the therapeutic means to be implemented will be adapted to this diagnosis.

TABLE 4

Organization of the multitest (distribution of the probes in the wells)

| Strip R1 | | Strip R2 | | Strip R2a | |
|---|---|---|---|---|---|
| C+ | SEQ ID NO: 1 | C + (B) | SEQ ID NO: 9 | C + (B) | SEQ ID NO: 9 |
| C− | SEQ ID NO: 2 | B27 | SEQ ID NO: 10 | B27 | SEQ ID NO: 10 |
| 4 | SEQ ID NO: 3 | 1 | SEQ ID NO: 11 | 1 | SEQ ID NO: 11 |
| QK71 | SEQ ID NO: 4 | 52 | SEQ ID NO: 12 | 52 | SEQ ID NO: 12 |
| IDE71 | SEQ ID NO: 5 | 2 | SEQ ID NO: 13 | 2 | SEQ ID NO: 13 |
| E74 | SEQ ID NO: 6 | 7 + 9 | SEQ ID NO: 14 | 3 | SEQ ID NO: 19 |
| QR71 | SEQ ID NO: 7 | 10 | SEQ ID NO: 15 | 10 | SEQ ID NO: 7 |
| S57 | SEQ ID NO: 8 | 8 + 12 | SEQ ID NO: 16 | 7 + 9 + 8 + 12 | SEQ ID NOs: 14 and 16 |

Strip R1 comprises a positive control (SEQ ID NO: 1) which makes it possible to detect all the alleles of the DRB1* gene, which makes it possible to verify that the region of interest between the primers P1 and P2 described in Table 1 was indeed that amplified. The negative control (SEQ ID NO: 2) has no diagnostic objective, it is present only to satisfy certain standards. This sequence is absolutely not specific for HLA, and corresponds to a random sequence which is not found in HLA genes.

SEQ ID NO: 3 allows the typing of the set of alleles which constitutes the DRB1*gr04 group. It allows the identification of all the DRB1*gr04 alleles, these alleles belonging to the group defined by HLA-typing techniques using serology, such as the DR4 group. It is a low-resolution probe, i.e. many alleles can be recognized with this probe.

SEQ ID NOs: 4 to 8 allow, themselves, the subtyping of some of the alleles which constitute the DRB1*gr04 group, specifying the allele(s) which share(s) a particular sequence. They are high-resolution probes, i.e. a few alleles, or even a single allele, can be recognized with one of these probes.

All these probes are used to detect the alleles containing the shared epitope, which are associated with genetic pre- In the case of strip 2a, the same configuration as strip R2 is substantially repeated, with the exception of two modifications.

Firstly, two reactions are grouped together. Thus, a single well contains within it two different probes, namely SEQ ID NO: 14 and SEQ ID NO: 16.

The well thus freed makes it possible to add a new probe, SEQ ID NO: 19, which is associated with the presence of DRB1*03 alleles (DR3). It is, in fact, judicious to be able to identify, in an independent manner, this group of DRB1*03 alleles, which is found to be associated with other diseases, such as lupus erythematosus disseminatus, collagen disease, Sjögren's syndrome or insulin-dependent diabetes for example.

4° Preparation of the Reagents for Analyzing the Amplicons Prepared:

The principle of reverse hybridization used is that described in document WO-A-93/02213 of the applicant, the content of which is considered to be contained in our patent application. Briefly, the specific capture probes are absorbed passively onto the polystyrene of the wells of strips assembled into microplates, by virtue of a modification of their 5' end (presence of an —NH$_2$ function). The detection probes are oligonucleotides covalently coupled to the HRP (horse radish peroxydase) enzyme by virtue of a modification of their 5' end (presence of an —NH$_2$ function). The composition of the hybridization buffer was modified as follows:

75 mM Na$_2$HPO$_4$.2H$_2$O, 25 mM NaH$_2$PO$_4$.H$_2$O, pH 6.8, 500 mM NaCl,

2% PEG 4000, 0.65% of Tween 20, 0.1% of gelatin, 0.14 g/l of sonicated DNA, 0.001% of ciprofloxacin hydrochloride, and 0.02% of bromonitrodioxane.

A multitest consists of a strip R1 and a strip R2 or R2a, as described in Table 4.

5°) Procedure:

1) Denaturation of the amplicons: 10 μl of denaturing reagent (2N NaOH) are added to 100 μl of prepared amplicon solution. Incubation for 5 minutes at 18–25° C.

2) Addition of 2 ml of hybridization buffer and of 0.2 ml of solution containing the detection probes.

3) Distribution of the mixture, in a proportion of 100 μl in each of the sixteen sensitized wells corresponding to a multitest. Cover with a self-adhesive sheet.

4) Incubation for 60 minutes in an incubator at 37° C. (35–39° C.).

5) Removal of the nonhybridized material by washing at 18–25° C.

6) Revelation of the enzymatic reaction by distributing 100 μl per well of substrate solution (OPD, orthophenylenediamine). Incubate for 20 minutes at 18–25° C. in the dark.

7) Reading of results: direct or recording of optical densities (reading at 492 nm).

8) Interpretation of the results.

II—EXAMPLES AND RESULTS

The results obtained with various samples with known HLA typing are shown below:

1°) First Sample:

The following two tables 5 and 6 represent the results obtained with two strips R1 and R2.

TABLE 5

| Strip R1 | | |
|---|---|---|
| Strip R1 | OD × 1000 | +/− |
| SEQ ID NO: 1 | >2500 | + |
| SEQ ID NO: 2 | — | − |
| SEQ ID NO: 3 | 898 | + |
| SEQ ID NO: 4 | 256 | + |
| SEQ ID NO: 5 | 1 | − |
| SEQ ID NO: 6 | 0 | − |
| SEQ ID NO: 7 | 10 | − |
| SEQ ID NO: 8 | 9 | − |

TABLE 6

| Strip R2 | | |
|---|---|---|
| Strip R2 | OD × 1000 | +/− |
| SEQ ID NO: 9 | >2500 | + |
| SEQ ID NO: 10 | 0 | − |
| SEQ ID NO: 11 | 0 | − |
| SEQ ID NO: 12 | 0 | − |
| SEQ ID NO: 13 | 2044 | + |
| SEQ ID NO: 14 | 0 | − |
| SEQ ID NO: 15 | 1 | − |
| SEQ ID NO: 16 | 3 | − |

Because a strip R2 is used, two analyses are possible.

Firstly, the HLA-DR analysis shows that:

the SEQ ID NO: 1 probe is positive: the HLA-DR amplification and the hybridization test have functioned correctly, the SEQ ID NO: 3 and SEQ ID NO: 4 probes are positive: a DRB1*gr0401 allele is present, and the SEQ ID NO: 13 probe is positive: a DRB1*02 allele is present.

In conclusion, a single allele for susceptibility to rheumatoid arthritis (DRB1*gr0401) is present, the second allele being DRB1*02 which is neutral with respect to rheumatoid arthritis.

Secondly, the HLA-B analysis shows that:

the SEQ ID NO: 9 probe is positive: the HLA-B amplification and hybridization test have functioned correctly, and the SEQ ID NO: 10 probe is negative: the B*27 allele is absent.

The patient whose sample was tested is not susceptible to ankylosing spondylitis.

The HLA typing of this first sample was:

HLA-DRB1*gr0401/1602, and

HLA-B*5701.

2°) Second Sample:

The following two tables 7 and 8 represent the results obtained with two strips R1 and R2.

TABLE 7

| Strip R1 | | |
|---|---|---|
| Strip R1 | OD × 1000 | +/− |
| SEQ ID NO: 1 | >2500 | + |
| SEQ ID NO: 2 | 0 | − |
| SEQ ID NO: 3 | 261 | + |
| SEQ ID NO: 4 | 0 | − |
| SEQ ID NO: 5 | 312 | + |
| SEQ ID NO: 6 | 0 | − |
| SEQ ID NO: 7 | 4 | − |
| SEQ ID NO: 8 | 0 | − |

TABLE 8

| Strip R2 | | |
|---|---|---|
| Strip R2 | OD × 1000 | +/− |
| SEQ ID NO: 9 | >2500 | + |
| SEQ ID NO: 10 | 0 | − |
| SEQ ID NO: 11 | 0 | − |
| SEQ ID NO: 12 | 0 | − |
| SEQ ID NO: 13 | 2300 | − |
| SEQ ID NO: 14 | 0 | − |
| SEQ ID NO: 15 | 0 | − |
| SEQ ID NO: 16 | 0 | − |

There are four positive probes, which are:

the SEQ ID NO: 1 probe: the HLA-DR amplification and the hybridization test have functioned correctly, the SEQ ID NO: 3 probe: at least one DRB1*gr04 allele is present, the SEQ ID NO: 5 probe: at least one DRB1*gr0402 allele is present, and the SEQ ID NO: 9 probe: at least one B* allele is present, but B*27 is not present since SEQ ID NO: 10 is negative.

A DR4 allele is therefore present, but this allele is of a subtype which is not involved in genetic susceptibility to RA (DRB1*gr0402). Identification of the second allele makes it possible to establish that it is DRB1*02.

The HLA typing of this third sample was:

HLA-DRB1*gr0402/02, and

HLA-B other than B*27.

3°) Third Sample:

The following two tables 9 and 10 represent the results obtained with two strips R1 and R2.

TABLE 9

| Strip R1 | | |
| --- | --- | --- |
| Strip R1 | OD × 1000 | +/− |
| SEQ ID NO: 1 | >2500 | + |
| SEQ ID NO: 2 | — | − |
| SEQ ID NO: 3 | 4 | − |
| SEQ ID NO: 4 | 21 | − |
| SEQ ID NO: 5 | 1145 | + |
| SEQ ID NO: 6 | 0 | − |
| SEQ ID NO: 7 | 8 | − |
| SEQ ID NO: 8 | 0 | − |

TABLE 10

| Strip R2 | | |
| --- | --- | --- |
| Strip R2 | OD × 1000 | +/− |
| SEQ ID NO: 9 | >2500 | + |
| SEQ ID NO: 10 | 2228 | + |
| SEQ ID NO: 11 | 12 | − |
| SEQ ID NO: 12 | 1278 | + |
| SEQ ID NO: 13 | 877 | + |
| SEQ ID NO: 14 | 0 | − |
| SEQ ID NO: 15 | 0 | − |
| SEQ ID NO: 16 | 5 | − |

Like the previous two examples, two analyses are possible.

Firstly, the HLA-DR analysis shows that:

the SEQ ID NO: 1 probe is positive: the HLA-DR amplification and the hybridization test have functioned correctly, the SEQ ID NO: 3 probe is negative: no DRB1*gr04 allele is present, the SEQ ID NO: 5 and SEQ ID NO: 12 probes are positive: a DRB1*11 or 13 allele is present, and the SEQ ID NO: 13 probe is positive: a DRB1*02 allele is present.

In conclusion, there is no allele for susceptibility to rheumatoid arthritis, the two DR alleles were, however, identified at the generic level.

Secondly, the HLA-B analysis shows that:

the SEQ ID NO: 9 probe is positive: the HLA-B amplification and the hybridization test have functioned correctly, and the SEQ ID NO: 10 probe is positive: at least one B*27 allele is present.

The HLA typing of this third sample was:

HLA-DRB1*02/1301, and

HLA-B*27.

4°) Fourth Sample:

The following two tables 11 and 12 represent the results obtained with two strips R1 and R2a.

The configuration with two strips R1 and especially R2a (see Table 4) makes it possible, in addition to the analysis of genetic susceptibility to rheumatoid arthritis and to ankylosing spondylitis, to more clearly analyze genetic susceptibility to lupus erythematosus disseminatus, to collagen diseases, to Sjögren's syndrome and to other diseases encountered during a rheumatology consultation. This is carried out by combining, in a single well, SEQ ID NOs: 14 and 16, which contain probes 7, 8, 9 and 12, the specificities of which are described in Table 3.

TABLE 11

| Strip R1 | | |
| --- | --- | --- |
| Strip R1 | OD × 1000 | +/− |
| SEQ ID NO: 1 | >2500 | + |
| SEQ ID NO: 2 | 0 | − |
| SEQ ID NO: 3 | 275 | + |
| SEQ ID NO: 4 | 241 | + |
| SEQ ID NO: 5 | 0 | − |
| SEQ ID NO: 6 | 0 | − |
| SEQ ID NO: 7 | 0 | − |
| SEQ ID NO: 8 | 0 | − |

TABLE 12

| Strip R2 | | |
| --- | --- | --- |
| Strip R2 | OD × 1000 | +/− |
| SEQ ID NO: 9 | >2500 | + |
| SEQ ID NO: 10 | 0 | − |
| SEQ ID NO: 11 | 0 | − |
| SEQ ID NO: 12 | 1832 | + |
| SEQ ID NO: 13 | 2 | − |
| SEQ ID NO: 14 | 849 | + |
| SEQ ID NO: 15 | 0 | − |
| SEQ ID NOS: 14 + 16 | 67 | − |

There are six positive probes, which are:

the SEQ ID NO: 1 probe: the HLA-DR amplification and the hybridization test have functioned correctly, the SEQ ID NO: 3 probe: at least one DRB1*gr04 allele is present, the SEQ ID NO: 4 probe: at least one DRB1*gr0401 allele is present, the SEQ ID NO: 9 probe: at least one B* allele is present, but B*27 is not present since SEQ ID NO: 10 is negative, the SEQ ID NO: 12 probe: at least one DRB1*03, 11, 13 or 14 allele is present, and the SEQ ID NO: 19 probe: at least one DRB1*03 allele is present.

An allele for genetic susceptibility to rheumatoid arthritis is therefore present, due to the existence of the DRB1*gr0401 allele, as is an allele for genetic susceptibility to lupus erythematosus disseminatus, due to the existence of the DRB1*03 allele, in this patient. There is no allele concerning B*27.

The HLA typing of this fourth sample was:
HLA-DRB1*gr0401/0301, and
HLA-B other than B*27.

III—OPTIMIZATION OF THE RESULTS

The objective was to improve the conditions under which the amplification should be carried out. The optimal conditions are given in Table 13 below.

TABLE 13

Simultaneous and optimized amplification of the regions of interest HLA-DR and HLA-B

| | |
|---|---|
| Primers | P1 (5' primer-DR): SEQ ID NO: 20 |
| | CCG GAT CCT TCG TGT CCC CAC AGC ACG (5' > 3') |
| | P2 (3' primer-DR): SEQ ID NO: 21 |
| | TCG CCG CTG CAC TGT GAA G (5' > 3') |
| | P3 (5' primer-B): SEQ ID NO: 25 |
| | GGG AGG AGC GAG GGG ACC GCA (5' > 3') |
| | P4 (3' primer-B): SEQ ID NO: 26 |
| | ATC TCG GAC CCG GAG ACT CG (5' > 3') |
| Reaction mixture | 10X TEMAG buffer (*): 10 µl |
| | dNTPs (20 mM): 1 µl (0.2 mM final) |
| | P1 (40 µM): 1 µl (0.4 µM final) |
| | P2 (40 µM): 1 µl (0.4 µM final) |
| | P3 (30 µM): 1 µl (0.3 µM final) |
| | P4 (30 µM): 1 µl (0.3 µM final) |
| | AmpliTaq (5 U/µl): 0.5 µl (2.5 U) |
| | DNA: 100–500 ng |
| | H$_2$O: QS for 100 µl |
| Amplification program | (5 min at 96° C.) + 10 × (10 sec at 98° C. + 30 sec at 65° C. + 30 sec at 72° C.) + 30 × (20 sec at 96° C. + 30 sec at 62° C. + 30 sec at 72° C.) |

The differences between the amplification conditions of Table 1 and of Table 9 therefore lie in the choice of the slightly modified primers P3 and P4, new concentrations of primers P1, P2, P3 and P4 and a temperature variation in the amplification program. The introduction of these modifications into the results is specified in Tables 14, 15 and 16, which each correspond to a different patient sample.

TABLE 14

Comparative study of the first sample

| | Initial conditions | Optimized primers | Optimized amplification | Optimized primers and amplification |
|---|---|---|---|---|
| SEQ ID NO: 1 | >2500 | >2500 | >2500 | >2500 |
| SEQ ID NO: 2 | 0 | 0 | 0 | 0 |
| SEQ ID NO: 3 | 97 | 171 | 202 | 365 |
| SEQ ID NO: 4 | 52 | 95 | 59 | 42 |
| SEQ ID NO: 5 | 959 | 1552 | 966 | 1472 |
| SEQ ID NO: 6 | 0 | 0 | 0 | 0 |
| SEQ ID NO: 7 | 17 | 44 | 31 | 45 |
| SEQ ID NO: 8 | 0 | 16 | 0 | 3 |
| SEQ ID NO: 9 | 1237 | 1708 | 1627 | 1792 |
| SEQ ID NO: 10 | 211 | 363 | 394 | 414 |
| SEQ ID NO: 11 | 3 | 0 | 0 | 0 |
| SEQ ID NO: 12 | 882 | 895 | 737 | 791 |
| SEQ ID NO: 13 | 0 | 0 | 0 | 0 |
| SEQ ID NO: 14 | 0 | 0 | 0 | 0 |
| SEQ ID NO: 15 | 0 | 0 | 0 | 0 |
| SEQ ID NO: 16 | 0 | 0 | 0 | 0 |

The typing of this first sample is DRB1*gr0404/52.

TABLE 15

Comparative study of the second sample

| | Initial conditions | Optimized primers | Optimized amplification | Optimized primers and amplification |
|---|---|---|---|---|
| SEQ ID NO: 1 | 789 | 1335 | 1240 | 1914 |
| SEQ ID NO: 2 | 0 | 0 | 0 | 0 |
| SEQ ID NO: 3 | 353 | 649 | 635 | 944 |
| SEQ ID NO: 4 | 14 | 49 | 45 | 102 |
| SEQ ID NO: 5 | 104 | 232 | 228 | 463 |
| SEQ ID NO: 6 | 0 | 0 | 0 | 0 |
| SEQ ID NO: 7 | 0 | 0 | 0 | 0 |
| SEQ ID NO: 8 | 0 | 0 | 0 | 0 |
| SEQ ID NO: 9 | 1822 | >2500 | 2120 | 2240 |
| SEQ ID NO: 10 | 0 | 0 | 0 | 0 |
| SEQ ID NO: 11 | 0 | 0 | 0 | 0 |
| SEQ ID NO: 12 | 0 | 0 | 0 | 0 |
| SEQ ID NO: 13 | 1 | 5 | 2 | 1 |
| SEQ ID NO: 14 | 0 | 0 | 0 | 0 |
| SEQ ID NO: 15 | 0 | 0 | 0 | 0 |
| SEQ ID NO: 16 | 0 | 0 | 3 | 0 |

The typing of this second sample is DRB1*gr0401/gr0402.

TABLE 16

Comparative study of the third sample

| | Initial conditions | Optimized primers | Optimized amplification | Optimized primers and amplification |
|---|---|---|---|---|
| SEQ ID NO: 1 | 615 | 1156 | 1052 | 2098 |
| SEQ ID NO: 2 | 0 | 0 | 0 | 0 |
| SEQ ID NO: 3 | 429 | 691 | 679 | 1381 |
| SEQ ID NO: 4 | 0 | 0 | 0 | 0 |
| SEQ ID NO: 5 | 0 | 0 | 0 | 0 |
| SEQ ID NO: 6 | 8 | 23 | 17 | 66 |
| SEQ ID NO: 7 | 14 | 26 | 21 | 66 |
| SEQ ID NO: 8 | 64 | 174 | 131 | 405 |
| SEQ ID NO: 9 | 1348 | 2377 | 2089 | 2191 |
| SEQ ID NO: 10 | 296 | 622 | 567 | 490 |
| SEQ ID NO: 11 | 0 | 0 | 0 | 0 |
| SEQ ID NO: 12 | 0 | 0 | 0 | 0 |
| SEQ ID NO: 13 | 3 | 0 | 1 | 0 |
| SEQ ID NO: 14 | 0 | 0 | 0 | 0 |
| SEQ ID NO: 15 | 0 | 0 | 0 | 0 |
| SEQ ID NO: 16 | 0 | 2 | 0 | 0 |

The typing of this third sample is DRB1*gr0403/gr0405.

All these values are OD values multiplied by one thousand (OD×1000). Since the maximum readable value is 2.5, when the number is greater than this value, the value is simply indicated as being greater than 2500 (>2500).

It is noted that all the highest significant values have been emphasized by placing them in bold. This involves only the positive probes. For the first sample, of the seven significant values, all of them are derived from the conditions optimized with respect to the initial conditions. Three are associated with optimization of the primers and four are associated with optimization of the primers and of the amplification. For the second sample, of the five significant values, all of them are derived from the conditions optimized with respect to the initial conditions. One is associated with optimization of the primers and four are associated with optimization of the primers and of the amplification. For the third sample, of the seven significant values, all of them are derived from the conditions optimized with respect to the initial conditions.

Two are associated with optimization of the primers and five are associated with optimization of the primers and of the amplification.

Optimization of the amplification alone is less worthwhile than optimization of the primers alone or optimization of the primers and of the amplification. However, it is noted that, of the sequences corresponding to the nineteen significant values, eighteen are in favor of optimization of the amplification with respect to the initial conditions.

In comparing the amplification techniques according to Table 1 and according to Table 13, it is seen that the amplification is more efficient when the final concentration of primers for amplifying the sequence corresponding to the DRB1*gr04 groups of alleles is higher than the final concentration of primers for amplifying the sequence corresponding to the B27 allele.

IV—IMPROVEMENTS

In certain cases, ambiguities may appear. Thus, since the primers are not specific for DR4, other alleles are amplified, which may cause difficulties in interpretation. This is, for example, the case in the three examples below; the only solution is then to carry out a more highly targeted amplification on DR4, using particular primers as described in Table 17 below:

TABLE 17

| | Targeted amplification of a region of interest HLA-DR |
|---|---|
| Primers | P5 (5' primer-DR): SEQ ID NO: 27<br>GTT TCT TGG AGC AGG TTA AAC (5' > 3')<br>P2 (3' primer-DR): SEQ ID NO: 21<br>TCG CCG CTG CAC TGT GAA G (5' > 3') |
| Reaction mixture | Tris-HCl buffer, pH 8.3: 50 μM<br>dNTPs (20 mM): 1 μl (0.2 mM final)<br>P2 (30 μM): 1 μl (0.3 μM final)<br>P5 (30 μM): 1 μl (0.3 μM final)<br>AmpliTaq (5 U/μl): 0.3 μl (1.5 U)<br>DNA: 100–500 ng<br>H₂O: QS for 100 μl |
| Amplification program | (2 min at 95° C.) + 32 × (30 sec at 95° C. + 30 sec at 55° C. + 30 sec at 72° C.) + 30 × (20 sec at 96° C. + 30 sec at 62° C. + 30 sec at 72° C. + 7 min at 72° C.) |

The examples which show such ambiguities and the resolution thereof are as follows.

1°) First Sample:

TABLE 18

| Strip R1 | | |
|---|---|---|
| Strip R1 | OD × 1000 | +/− |
| SEQ ID NO: 1 | >2500 | + |
| SEQ ID NO: 2 | <50 | − |
| SEQ ID NO: 3 | 197 | + |
| SEQ ID NO: 4 | 182 | + |
| SEQ ID NO: 5 | 1692 | + |
| SEQ ID NO: 6 | 0 | − |
| SEQ ID NO: 7 | 11 | − |
| SEQ ID NO: 8 | 3 | − |

TABLE 19

| Strip R2 | | |
|---|---|---|
| Strip R2a | OD × 1000 | +/− |
| SEQ ID NO: 9 | >2500 | + |
| SEQ ID NO: 10 | 0 | − |
| SEQ ID NO: 11 | 2 | − |
| SEQ ID NO: 12 | 1519 | + |
| SEQ ID NO: 13 | 0 | − |
| SEQ ID NO: 14 | 0 | − |
| SEQ ID NO: 15 | 0 | − |
| SEQ ID NO: 16 | 0 | − |

In this case, it is not possible, without taking a risk, to differentiate, within the DRB1*gr04 group (SEQ ID NO: 3 is positive) between DRB1*gr0401 (SEQ ID NO: 4 is positive) and DRB1*gr0402 (SEQ ID NO: 5 is positive). The other allele is a gr52 (SEQ ID NO: 12 is positive). In addition, the crude figures tend to favor DRB1*gr0402, since SEQ ID NO: 5 has a positive value of 1692, whereas, for DRB1*gr0401, SEQ ID NO: 4 has a positive value of only 182.

Nevertheless, the second analysis will make it possible to differentiate these two alleles. This is clearly represented in Tables 20 and 21.

TABLE 20

| Strip R1 | | |
|---|---|---|
| Strip R1 | OD × 1000 | +/− |
| SEQ ID NO: 1 | 2181 | + |
| SEQ ID NO: 2 | <50 | − |
| SEQ ID NO: 3 | 1281 | + |
| SEQ ID NO: 4 | 200 | + |
| SEQ ID NO: 5 | 0 | − |
| SEQ ID NO: 6 | 0 | − |
| SEQ ID NO: 7 | 1 | − |
| SEQ ID NO: 8 | 0 | − |

TABLE 21

| Strip R2 | | |
|---|---|---|
| Strip R2a | OD × 1000 | +/− |
| SEQ ID NO: 9 | ND | ? |
| SEQ ID NO: 10 | ND | ? |
| SEQ ID NO: 11 | 0 | − |
| SEQ ID NO: 12 | 0 | − |
| SEQ ID NO: 13 | 0 | − |
| SEQ ID NO: 14 | 0 | − |
| SEQ ID NO: 15 | 0 | − |
| SEQ ID NO: 16 | 0 | − |

It is therefore clearly seen on this second analysis that it is DRB1*gr0401 (SEQ ID NO: 4 is positive), not DRB1*gr0402 (SEQ ID NO: 5 is negative). It is therefore possible to differentiate between DRB1*gr0401 and DRB1*gr0402, which is of considerable bearing, since these two alleles do not have the same impact on rheumatoid arthritis. Thus, DRB1*gr0401 is associated with genetic susceptibility to rheumatoid arthritis, and DRB1*gr0402 is associated with genetic resistance to rheumatoid arthritis.

The typing of this first sample is therefore DRB1*gr0401/gr52.

2°) Second Sample:

TABLE 22

| Strip R1 | | |
|---|---|---|
| Strip R1 | OD × 1000 | +/− |
| SEQ ID NO: 1 | >2500 | + |
| SEQ ID NO: 2 | <50 | − |
| SEQ ID NO: 3 | 193 | + |
| SEQ ID NO: 4 | 21 | − |
| SEQ ID NO: 5 | 0 | − |
| SEQ ID NO: 6 | 0 | − |
| SEQ ID NO: 7 | 72 | + |
| SEQ ID NO: 8 | 137 | + |

TABLE 23

| Strip R2 | | |
|---|---|---|
| Strip R2a | OD × 1000 | +/− |
| SEQ ID NO: 9 | >2500 | + |
| SEQ ID NO: 10 | 1 | − |
| SEQ ID NO: 11 | 1 | − |
| SEQ ID NO: 12 | 1827 | + |
| SEQ ID NO: 13 | 0 | − |
| SEQ ID NO: 14 | 0 | − |
| SEQ ID NO: 15 | 0 | − |
| SEQ ID NO: 16 | 3 | − |

In this case, it is not possible, without taking a risk, to differentiate, within the DRB1*gr04 group (SEQ ID NO: 3 is positive), between DRB1*gr0404 (SEQ ID NO: 7 is positive) and DRB1*gr0405 (SEQ ID NO: 7 and SEQ ID NO: 8 are both positive). The other allele is a gr52 (SEQ ID NO: 12 is positive).

Nevertheless, the second analysis will make it possible to differentiate these two alleles. This is clearly represented on Tables 24 and 25.

TABLE 24

| Strip R1 | | |
|---|---|---|
| Strip R1 | OD × 1000 | +/− |
| SEQ ID NO: 1 | >2500 | + |
| SEQ ID NO: 2 | <50 | − |
| SEQ ID NO: 3 | >2500 | + |
| SEQ ID NO: 4 | 0 | − |
| SEQ ID NO: 5 | 0 | − |
| SEQ ID NO: 6 | 0 | − |
| SEQ ID NO: 7 | 773 | + |
| SEQ ID NO: 8 | 560 | + |

TABLE 25

| Strip R2 | | |
|---|---|---|
| Strip R2a | OD × 1000 | +/− |
| SEQ ID NO: 9 | ND | ? |
| SEQ ID NO: 10 | ND | ? |
| SEQ ID NO: 11 | 0 | − |
| SEQ ID NO: 12 | 0 | − |
| SEQ ID NO: 13 | 0 | − |
| SEQ ID NO: 14 | 0 | − |

TABLE 25-continued

| Strip R2 | | |
|---|---|---|
| Strip R2a | OD × 1000 | +/− |
| SEQ ID NO: 15 | 0 | − |
| SEQ ID NO: 16 | 0 | − |

It is therefore clearly seen on this second analysis that it is DRB1*gr0405 (SEQ ID NO: 7 and SEQ ID NO: 8 are positive), whereas, if it was DRB1*gr0404 SEQ ID NO: 8 should have been negative. It is therefore possible to differentiate between DRB1*gr0404 and DRB1*gr0405, which has less of a bearing than the previous example since, according to current knowledge, these two alleles have the same impact on rheumatoid arthritis. Thus, DRB1*gr0404 and DRB1*gr0405 are both associated with genetic susceptibility to rheumatoid arthritis. Of course, the importance of this second analysis may vary if future knowledge proves one of these two alleles to have a more significant impact than the other.

The typing of this second sample is therefore DRB1*gr0405/gr52.

3°) Third Sample:

TABLE 26

| Strip R1 | | |
|---|---|---|
| Strip R1 | OD × 1000 | +/− |
| SEQ ID NO: 1 | >2500 | + |
| SEQ ID NO: 2 | <50 | − |
| SEQ ID NO: 3 | 237 | + |
| SEQ ID NO: 4 | 1 | − |
| SEQ ID NO: 5 | 0 | − |
| SEQ ID NO: 6 | 0 | − |
| SEQ ID NO: 7 | 156 | + |
| SEQ ID NO: 8 | 563 | + |

TABLE 27

| Strip R2 | | |
|---|---|---|
| Strip R2a | OD × 1000 | +/− |
| SEQ ID NO: 9 | >2500 | + |
| SEQ ID NO: 10 | 637 | + |
| SEQ ID NO: 11 | 2 | − |
| SEQ ID NO: 12 | 4 | − |
| SEQ ID NO: 13 | 0 | − |
| SEQ ID NO: 14 | 0 | − |
| SEQ ID NO: 15 | 0 | − |
| SEQ ID NO: 16 | 248 | + |

In this case, it is not possible, without taking a risk, to differentiate, within the DRB1*gr04 group (SEQ ID NO: 3 is positive), between DRB1*gr0404 (SEQ ID NO: 7 is positive) and DRB1*gr0405 (SEQ ID NO: 7 and SEQ ID NO: 8 are both positive). The other allele is a gr8+12 (SEQ ID NO: 16 is positive), which is neutral for rheumatoid arthritis or ankylosing spondylitis, according to current knowledge. It should also be noted that, unlike the previous two examples, a B*27 allele is present. The second analysis will once again make it possible to differentiate these two alleles. This is clearly represented in Tables 28 and 29.

TABLE 26

| Strip R1 | | |
|---|---|---|
| Strip R1 | OD × 1000 | +/− |
| SEQ ID NO: 1 | >2500 | + |
| SEQ ID NO: 2 | <50 | − |
| SEQ ID NO: 3 | 1453 | + |
| SEQ ID NO: 4 | 0 | − |
| SEQ ID NO: 5 | 0 | − |
| SEQ ID NO: 6 | 0 | − |
| SEQ ID NO: 7 | 467 | + |
| SEQ ID NO: 8 | 1 | + |

TABLE 27

| Strip R2 | | |
|---|---|---|
| Strip R2a | OD × 1000 | +/− |
| SEQ ID NO: 9 | ND | ? |
| SEQ ID NO: 10 | ND | ? |
| SEQ ID NO: 11 | 0 | − |
| SEQ ID NO: 12 | 0 | − |
| SEQ ID NO: 13 | 0 | − |
| SEQ ID NO: 14 | 0 | − |
| SEQ ID NO: 15 | 0 | − |
| SEQ ID NO: 16 | 0 | − |

It is therefore clearly seen on this second analysis that it is DRB1*gr0404, since SEQ ID NO: 7 is positive and SEQ ID NO: 8 is negative, whereas, if it was DRB1*gr0405, SEQ ID NO: 8 should have been positive, as in the previous example. It is therefore possible to differentiate between DRB1*gr0404 and DRB1*gr0405, which has less of a bearing than in the first example since these two alleles have the same impact on rheumatoid arthritis. Thus, DRB1*gr0404 and DRB1*gr0405 are both associated with genetic susceptibility to rheumatoid arthritis. However, the comments made for the second sample may be reiterated.

The typing of this third sample is therefore DRB1*gr0404/gr8+12, with at least one B*27 allele being present.

V—CONCLUSIONS

As these examples prove, the method claimed makes it possible to simultaneously carry out, in one- or two steps, a search for genetic susceptibility to rheumatoid arthritis, based on an analysis entirely dedicated to the information required by the clinician (DR1, DR4, DR10, DRB1*gr04 subtypes, presence of the motif QKRAA (SEQ ID NO: 28), QRRAA (SEQ ID NO: 29) and RRRAA (SEQ ID NO: 30), dose-effect) and also a search for HLA-B*27, often informative during a rheumatology consultation.

When a rheumatology consultation is carried out, the relevance of the HLA-DR and HLA-B27 information needs to be known. Simplicity, feasibility and rapidity of the test, with, consequently, a considerable financial impact, are the advantages of the method according to the invention.

BIBLIOGRAPHICAL REFERENCES INCORPORATED INTO THE PRESENT DESCRIPTION AS NEEDED

Baarsma, 1992:
Baarsma G S, Current Eye Researc, 1992, 11 suppl., 1–9
Benjamin, 1990:
Benjamin R, Parham P, Immunology Today, 1990, 11, 137–142, Guilt by association: HLA-B27 and ankylosing spondylitis
Brewerton, 1972:
Brewerton D A, Caffrey M, Hard F D et al, Lancet, 1973, 1, 904–907. Ankylosing spondylitis and HL-A27.
Dominguez, 1992:
Dominguez O, Coto E, Martinez-Naves E, Choo S Y, Lopez-Larrea C, Immunogenetics, 1992, 36, 277–282. Molecular typing of HLA-B27 alleles (RM H # 311)
Gregersen, 1986:
Gregersen P K, Shen M, Song Q L, Merryman P, Degar S, Seki T, Maccari J, Goldberg D, Murphy H, Schwenzer J, Wang C Y, Winchester R J, Nepom G T, Silver J, Proc. Natl. Acad. Sci. USA, 1986, 83, 2642–2646. Molecular diversity of HLA-DR4 haplotypes.
Gregersen, 1987:
Gregersen P K, Silver J, Winchester R J, Arthritis Rheum., 1987, 30, 1205–1213. The shared epitope hypothesis. An approach to understanding the molecular genetics of susceptibility to rheumatoid arthritis.
Hill, 1991:
Hill A V S et al, The Lancet, 1991, Mar. 16, 337, 640–642
Hiraiwa, 1990:
Hiraiwa A, Yamanaka K, Kwok W W, Mickelson E M, Masewicz S, Hansen J A, Radka S F, Nepom G T, Proc. Natl. Acad. Sci. USA, 1990, 87, 8051–8055. Structural requirements for recognition of the HLA-Dw14 class II epitope: a key HLA determinant associated with rheumatoid arthritis.
Khan, 1979:
Khan M A, Kushner I, Ballou S P et al, Lancet, 1979, 1, 921–922, Familial rheumatoid arthritis and HLA-DRW4.
Kirveskari, 1997:
Kirveskari J, Kellner H, Wuorela M, Soini H, Frankenberger B, Leirisalo-Repo M, Weiss E H, Granfors K, Br. J. Rheumatol., 1997, 36, 185–189, False-negative serological HLA-B27 typing results may be due to altered antigenic epitopes and can be detected by polymerase chain reaction.
Lawrence, 1970:
Lawrence J, Ann. Rheum. Dis., 1970, 29, 357–379
Nepom, 1989:
Nepom G T, Byers P, Seyfried C, Healey L A, Wilske K R, Stage D, Nepom BS, Arthritis Rheum. 1989, 32, 15–21. HLA genes associated with rheumatoid arthritis. Identification of susceptibility alleles using specific oligonucleotide probes.
Nepom, 1991:
Nepom G T, Erlich H, Annu. Rev. Immunol., 1991, 9, 493–525. MHC class-II molecules and autoimmunity.
Neumüller, 1993:
Neumüller J, Fischer M, Eberl R, Rheumatol. Int., 1993, 13, 163–167. Failure of the serological determination of HLA-B27 due to antigen masking in patients with ankylosing spondylitis.
Schlosstein, 1973:
Schlosstein L, Terasaki P I, Bluestone R, Pearson C M, N. Engl. J. Med., 1973, 288, 704–706. High association of a HL-antigen, w27, with ankylosing spondylitis.
Stastny, 1978:
Stastny P, N. Engl. J. Med., 1978, 298, 869–871. Association of the B-cell alloantigen DRw4 with rheumatoid arthritis.
Stastny, 1983:
Stastny P, Ball E J, Dry P J, Nunez G, Immunol. Rev., 1983, 70, 113–154. The human immune response region (HLA-D) and disease susceptibility.

Stastny, 1988:
Stastny P, Ball E, Kahn M, Olsen N, Pincus T, Gao X, Br. J. Rheumatol., 1988, 27, 132–138. HLA-DR4 and other genetic markers in rheumatoid arthritis.

Todd, 1988:
Todd J A, Acha-Orbea H, Bell J I, Chao N, Fronek Z, Jacob C O, McDermott M, Sinha A A, Timmerman L, McDevitt H O, Science, 1988, 240, 1003–1009.

Weiss, 1985:
Weiss E H, Kuon W, Doerner C, Lang M, Riethmüller G, Immunobiology, 1985, 170, 367–380, A molecular approach to analyze HLA and disease associations.

Wordsworth, 1989:
Wordsworth B P, Lanchbury J S, Sakkas L I, Welsh K I, Panayi G S, Bell J I, Proc. Natl. Acad. Sci. USA, 1989, 86, 10049–10053.

The invention claimed is:

1. A method for analyzing a patient's genetic predisposition to rheumatoid arthritis, said method comprising:
   (1) placing a liquid sample containing at least one type of amplicon, derived from the amplification of at least one polymorphic region of the HLA-DR locus of nucleic acid from said patient, in the presence of probes including:
      one or more specific "low-resolution" typing probe(s) having the ability to hybridize with the DRB 1*gr04 group of alleles,
      one or more specific "high-resolution" subtyping probe(s) associated with genetic susceptibility to rheumatoid arthritis and having the ability to hybridize with the following alleles: DRB1*0101, DRB1*gr0401, DRB1*gr0404, DRB1*gr0405, DRB1*gr0408 and DRB1*gr1402, and
      one or more specific "high-resolution" subtyping probe(s) associated with genetic resistance to rheumatoid arthritis and having the ability to hybridize with the following alleles: DRB1*gr0402, DRB1*gr0403, DRB1*gr0406 and DRB1*gr0407,
      wherein the high resolution subtyping probes make it possible to distinguish between allele(s) associated with susceptibility and allele(s) associated with resistance, to rheumatoid arthritis, according to whether or not they hybridize; and
   (2) determining the hybridization pattern between said sample and said probes to analyze the patient's genetic predisposition to rheumatoid arthritis.

2. The method as claimed in claim 1, said probes further comprising at least one low-resolution probe having the ability to hybridize with at least one allele selected from the group consisting of DRB1*01, DRB1*02, DRB1*03, DRB1*07, DRB1*08, DRB1*09, DRB1*10, DRB1*11, DRB1*12, DRB1*13 and DRB1*14.

3. The method as claimed in claim 1, wherein the probes comprise:
   the probe set forth in SEQ ID NO: 3, for DRB1*gr04 typing, and at least one of:
   (a) at least two probes associated with genetic susceptibility to rheumatoid arthritis, said probes including the probe set forth in SEQ ID NO: 4, for DRB1*gr0401 typing, and the probe set forth in SEQ ID NO: 7, for DRB1*0101, DRB1*gr0404, DRB1*gr0405, DRB1*04gr08 and DRB1*1402 typing, and
   (b) at least two probes associated with genetic resistance to rheumatoid arthritis, said probes including the probe set forth in SEQ ID NO: 5, for DRB1*gr0402 typing, and the probe set forth in SEQ ID NO: 6, for DRB1*gr0403, DRB1*gr0406 and DRB 1*gr0407 typing.

4. The method as claimed in claim 3, said probes further comprising the probe set forth in SEQ ID NO: 8, specific for DRB1*gr0405, said probe being associated with genetic susceptibility to rheumatoid arthritis.

5. The method as claimed in claim 1, wherein the probes comprise:
   the probe set forth in SEQ ID NO: 3, for DRB1*gr04 typing,
   at least two probes associated with genetic susceptibility to rheumatoid arthritis, said probes including the probe set forth in SEQ ID NO: 4, for DRB1*gr0401 typing, and the probe set forth in SEQ ID NO: 7, for DRB1*0101, DRB1*gr0404, DRB1*gr0405, DRB1*04gr08 and DRB1*1402 typing, and
   at least two probes associated with genetic resistance to rheumatoid arthritis, said probes including the probe set forth in SEQ ID NO: 5, for DRB1*gr0402 typing, and the probe set forth in SEQ ID NO: 6, for DRB1*gr0403, DRB1*gr0406 and DRB1*gr0407 typing.

6. The method as claimed in claim 2, wherein the low resolution probes are:
   the probe set forth in SEQ ID NO: 11, for the DRB1*01 group of alleles, and
   the probe set forth in SEQ ID NO: 15, for the DRB1*10 allele.

7. The method as claimed in claim 2, wherein the low resolution probes are:
   the probe set forth in SEQ ID NO: 13, for DRB1*02,
   the probe set forth in SEQ ID NO: 14, for DRB1*07 and DRB1*09,
   the probe set forth in SEQ ID NO: 16, for DRB1*08 and DRB1*12, and
   the probe set forth in SEQ ID NO: 12 for DRB 1*03, DRB 1*11, DRB 1*13 and DRB1*14.

8. The method as claimed in claim 1, wherein each low- or high-resolution probe specific for the alleles for genetic susceptibility to rheumatoid arthritis comprises one of the following characteristic motifs: QKRAA (SEQ ID NO: 28), QRRAA (SEQ ID NO: 29) or RRRAA (SEQ ID NO: 30).

9. The method as claimed in claim 1, said probes further comprising at least one control probe having the ability to hybridize with the set of DRB1 genes, to allow detection of all the DRB1 genes.

10. The method as claimed in claim 1, wherein a maximum of 38.9% of the bases of the same low-resolution or high-resolution probe are replaced with at least one analogous base.

11. The method as claimed in claim 1, wherein each specific low-resolution or high-resolution probe is placed in a well of a microtitration plate, independently of the other probes.

12. The method as claimed in claim 1, wherein all the reactions are carried out simultaneously.

13. The method as claimed in claim 1, wherein at least one amplification of the polymorphic region(s) of interest is carried out beforehand.

14. The method as claimed in claim 1, wherein amplification of the polymorphic region(s) of interest associated with HLA-DR and amplification of polymorphic region(s) of interest associated with HLA-B are carried out simultaneously, beforehand.

15. The method as claimed in claim 1, wherein, to obtain the amplicons, a first and a second amplification of at least one polymorphic region is carried out, the second amplification being more highly targeted than the first amplification, the more highly targeted region being a region of interest with respect to rheumatoid arthritis.

16. The method as claimed in claim 15, wherein the first amplification is carried out at the same time as, or prior to, the second, more highly targeted amplification.

17. The method as claimed in claim 15, comprising amplifying the polymorphic region of HLA-DR locus with SEQ ID NO: 27 primers in combination with SEQ ID NO: 21 primers.

18. The method as claimed in claim 14, comprising:

amplifying the polymorphic region of HLA-DR locus with SEQ ID NO: 20 primers in combination with SEQ ID NO: 21 primers, and amplifying HLA-B locus with SEQ ID NO: 22, SEQ ID NO: 23 and/or SEQ ID NO: 25 primers in combination with SEQ ID NO 24: and/or SEQ ID NO: 26 primers.

19. The method as claimed in claim 18, in which the final concentration of primers for amplifying the HLA-DR locus is higher than the final concentration of primers for amplifying the HLA-B locus.

20. The method as claimed in claim 9, wherein the control probe has the sequence set forth in SEQ ID NO: 1.

21. The method as claimed in claim 10, wherein the at least one analogous base is inosine.

* * * * *

SEQUENCE LISTING

```
<160> NUMBER OF SEQ ID NOS: 30

<210> SEQ ID NO 1
<211> LENGTH: 18
<212> TYPE: DNA
<213> ORGANISM: Homo sapiens

<400> SEQUENCE: 1
ttcgacagcg acgtgggg                                                  18

<210> SEQ ID NO 2
<211> LENGTH: 20
<212> TYPE: DNA
<213> ORGANISM: Homo sapiens

<400> SEQUENCE: 2
tatgaaactt atggggatac                                                20

<210> SEQ ID NO 3
<211> LENGTH: 16
<212> TYPE: DNA
<213> ORGANISM: Homo sapiens

<400> SEQUENCE: 3
gatacttcta tcacca                                                    16

<210> SEQ ID NO 4
<211> LENGTH: 15
<212> TYPE: DNA
<213> ORGANISM: Homo sapiens
<220> FEATURE:
<221> NAME/KEY: misc_feature
<222> LOCATION: (9)..(9)
<223> OTHER INFORMATION: g or i
<220> FEATURE:
<221> NAME/KEY: misc_feature
<222> LOCATION: (13)..(13)
<223> OTHER INFORMATION: g or i

<400> SEQUENCE: 4
gagcagaanc ggncc                                                     15

<210> SEQ ID NO 5
<211> LENGTH: 15
<212> TYPE: DNA
<213> ORGANISM: Homo sapiens
<220> FEATURE:
<221> NAME/KEY: misc_feature
<222> LOCATION: (12)..(12)
<223> OTHER INFORMATION: g or i

<400> SEQUENCE: 5
ctggaagacg ancgg                                                     15

<210> SEQ ID NO 6
```

```
<211> LENGTH: 18
<212> TYPE: DNA
<213> ORGANISM: Homo sapiens
<220> FEATURE:
<221> NAME/KEY: misc_feature
<222> LOCATION: (5)..(5)
<223> OTHER INFORMATION: g or i
<220> FEATURE:
<221> NAME/KEY: misc_feature
<222> LOCATION: (7)..(7)
<223> OTHER INFORMATION: g or i
<220> FEATURE:
<221> NAME/KEY: misc_feature
<222> LOCATION: (10)..(10)
<223> OTHER INFORMATION: g or i
<220> FEATURE:
<221> NAME/KEY: misc_feature
<222> LOCATION: (13)..(13)
<223> OTHER INFORMATION: c or i
<220> FEATURE:
<221> NAME/KEY: misc_feature
<222> LOCATION: (15)..(15)
<223> OTHER INFORMATION: g or i
<220> FEATURE:
<221> NAME/KEY: misc_feature
<222> LOCATION: (17)..(17)
<223> OTHER INFORMATION: g or i
<220> FEATURE:
<221> NAME/KEY: misc_feature
<222> LOCATION: (18)..(18)
<223> OTHER INFORMATION: g or i

<400> SEQUENCE: 6
agcanangcn ggncnann                                          18

<210> SEQ ID NO 7
<211> LENGTH: 18
<212> TYPE: DNA
<213> ORGANISM: Homo sapiens
<220> FEATURE:
<221> NAME/KEY: misc_feature
<222> LOCATION: (9)..(9)
<223> OTHER INFORMATION: g or i
<220> FEATURE:
<221> NAME/KEY: misc_feature
<222> LOCATION: (11)..(12)
<223> OTHER INFORMATION: c or i
<220> FEATURE:
<221> NAME/KEY: misc_feature
<222> LOCATION: (13)..(13)
<223> OTHER INFORMATION: g or i
<220> FEATURE:
<221> NAME/KEY: misc_feature
<222> LOCATION: (15)..(15)
<223> OTHER INFORMATION: g or i

<400> SEQUENCE: 7
cagaggcgng nnncngtg                                          18

<210> SEQ ID NO 8
<211> LENGTH: 15
<212> TYPE: DNA
<213> ORGANISM: Homo sapiens

<400> SEQUENCE: 8
gcctagcgcc gagta                                             15

<210> SEQ ID NO 9
<211> LENGTH: 23
<212> TYPE: DNA
<213> ORGANISM: Homo sapiens

<400> SEQUENCE: 9
```
aaatacctca tggagtggga gcc                           23

<210> SEQ ID NO 10
<211> LENGTH: 18
<212> TYPE: DNA
<213> ORGANISM: Homo sapiens
<220> FEATURE:
<221> NAME/KEY: misc_feature
<222> LOCATION: (7)..(7)
<223> OTHER INFORMATION: g or i
<220> FEATURE:
<221> NAME/KEY: misc_feature
<222> LOCATION: (13)..(13)
<223> OTHER INFORMATION: g or i

<400> SEQUENCE: 10
tgccttngcc ttncagat                                 18

<210> SEQ ID NO 11
<211> LENGTH: 18
<212> TYPE: DNA
<213> ORGANISM: Homo sapiens

<400> SEQUENCE: 11
tggcagctta agtttgaa                                 18

<210> SEQ ID NO 12
<211> LENGTH: 16
<212> TYPE: DNA
<213> ORGANISM: Homo sapiens

<400> SEQUENCE: 12
tactctacgt ctgagt                                   16

<210> SEQ ID NO 13
<211> LENGTH: 17
<212> TYPE: DNA
<213> ORGANISM: Homo sapiens

<400> SEQUENCE: 13
cagcctaaga gggagtg                                  17

<210> SEQ ID NO 14
<211> LENGTH: 18
<212> TYPE: DNA
<213> ORGANISM: Homo sapiens
<220> FEATURE:
<221> NAME/KEY: misc_feature
<222> LOCATION: (1)..(1)
<223> OTHER INFORMATION: c or i
<220> FEATURE:
<221> NAME/KEY: misc_feature
<222> LOCATION: (6)..(6)
<223> OTHER INFORMATION: g or i
<220> FEATURE:
<221> NAME/KEY: misc_feature
<222> LOCATION: (11)..(11)
<223> OTHER INFORMATION: c or i

<400> SEQUENCE: 14
naggtngaca ncgtgtgc                                 18

<210> SEQ ID NO 15
<211> LENGTH: 15
<212> TYPE: DNA
<213> ORGANISM: Homo sapiens

```
<400> SEQUENCE: 15
ggaggaggtt aagtt                                                      15

<210> SEQ ID NO 16
<211> LENGTH: 14
<212> TYPE: DNA
<213> ORGANISM: Homo sapiens
<220> FEATURE:
<221> NAME/KEY: misc_feature
<222> LOCATION: (10)..(10)
<223> OTHER INFORMATION: t or i

<400> SEQUENCE: 16
ctctacgggn gagt                                                       14

<210> SEQ ID NO 17
<211> LENGTH: 16
<212> TYPE: DNA
<213> ORGANISM: Homo sapiens

<400> SEQUENCE: 17
gaacagccag aaggac                                                     16

<210> SEQ ID NO 18
<211> LENGTH: 19
<212> TYPE: DNA
<213> ORGANISM: Homo sapiens

<400> SEQUENCE: 18
ctcgctctgg ttgtagtag                                                  19

<210> SEQ ID NO 19
<211> LENGTH: 16
<212> TYPE: DNA
<213> ORGANISM: Homo sapiens
<220> FEATURE:
<221> NAME/KEY: misc_feature
<222> LOCATION: (14)..(14)
<223> OTHER INFORMATION: t or i

<400> SEQUENCE: 19
ccgggtggac aacnac                                                     16

<210> SEQ ID NO 20
<211> LENGTH: 27
<212> TYPE: DNA
<213> ORGANISM: Homo sapiens

<400> SEQUENCE: 20
ccggatcctt cgtgtcccca cagcacg                                         27

<210> SEQ ID NO 21
<211> LENGTH: 19
<212> TYPE: DNA
<213> ORGANISM: Homo sapiens

<400> SEQUENCE: 21
tcgccgctgc actgtgaag                                                  19

<210> SEQ ID NO 22
<211> LENGTH: 22
<212> TYPE: DNA
<213> ORGANISM: Homo sapiens

<400> SEQUENCE: 22
```

```
gggaggagcg aggggacccc ag                                      22

<210> SEQ ID NO 23
<211> LENGTH: 22
<212> TYPE: DNA
<213> ORGANISM: Homo sapiens

<400> SEQUENCE: 23
gggaggagcg aggggaccgc ag                                      22

<210> SEQ ID NO 24
<211> LENGTH: 18
<212> TYPE: DNA
<213> ORGANISM: Homo sapiens

<400> SEQUENCE: 24
atctcggacc cggagact                                           18

<210> SEQ ID NO 25
<211> LENGTH: 11
<212> TYPE: DNA
<213> ORGANISM: Homo sapiens

<400> SEQUENCE: 25 agggga ccgc a                                                 11

<210> SEQ ID NO 26
<211> LENGTH: 20
<212> TYPE: DNA
<213> ORGANISM: Homo sapiens

<400> SEQUENCE: 26
atctcggacc cggagactcg                                         20

<210> SEQ ID NO 27
<211> LENGTH: 21
<212> TYPE: DNA
<213> ORGANISM: Homo sapiens

<400> SEQUENCE: 27
gtttcttgga gcaggttaaa c                                       21

<210> SEQ ID NO 28
<211> LENGTH: 5
<212> TYPE: PRT
<213> ORGANISM: Artificial Sequence
<220> FEATURE:
<223> OTHER INFORMATION: Motif

<400> SEQUENCE: 28

Gln Lys Arg Ala Ala
1               5

<210> SEQ ID NO 29
<211> LENGTH: 5
<212> TYPE: PRT
<213> ORGANISM: Artificial Sequence
<220> FEATURE:
<223> OTHER INFORMATION: Motif

<400> SEQUENCE: 29

Gln Arg Arg Ala Ala
1               5
```

```
<210> SEQ ID NO 30
<211> LENGTH: 5
<212> TYPE: PRT
<213> ORGANISM: Artificial Sequence
<220> FEATURE:
<223> OTHER INFORMATION: Motif

<400> SEQUENCE: 30

Arg Arg Arg Ala Ala
1               5
```